US00PP18294P3

(12) United States Plant Patent
Dirr

(10) Patent No.: US PP18,294 P3
(45) Date of Patent: Dec. 11, 2007

(54) ***HYDRANGEA MACROPHYLLA* PLANT NAMED 'HYMMAD I'**

(50) Latin Name: *Hydrangea macrophylla*
Varietal Denomination: HYMMAD I

(75) Inventor: Michael A. Dirr, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 84 days.

(21) Appl. No.: 11/348,515

(22) Filed: Feb. 6, 2006

(65) Prior Publication Data

US 2007/0186317 P1 Aug. 9, 2007

(51) Int. Cl.
*A01H 5/00* (2006.01)

(52) U.S. Cl. ..... Plt./250

(58) Field of Classification Search ..... None
See application file for complete search history.

(56) References Cited

U.S. PATENT DOCUMENTS

PP16,204 P2 * 1/2006 Arts ..... Plt./250

* cited by examiner

*Primary Examiner*—Wendy C. Haas
(74) *Attorney, Agent, or Firm*—Greenlee Winner and Sullivan PC

(57) ABSTRACT

*Hydrangea macrophylla,* 'HYMMAD I' has pure white mophead inflorescences that remain white in the presence and absence of aluminum. Inflorescences mature to a iridescent lime green. The habit is rounded with strong stems that hold the flowers upright. The lustrous, dark green leaves are highly mildew resistant.

4 Drawing Sheets

Botanical classification: *Hydrangea macrophylla.*
Varietal denomination: 'HYMMAD I'.

BACKGROUND OF THE INVENTION

The present invention relates to a new and distinct cultivar of *Hydrangea macrophylla,* a member of the Hydrangeaceae family, hereinafter referred to as 'HYMMAD I'. This cultivar is grown primarily as an ornamental for landscape use and for use as a potted plant, fresh cut and dried flowers. The cultivar originated from open-pollination of *Hydrangea macrophylla* 'White Wave' (non-patented), the pollen donor being unknown. It was selected at the University of Georgia, Athens, Ga. in 2002, from the progeny seedlings of this open pollination by continued evaluation for pure white mophead flowers unaffected by the absence or presence of aluminum (Al), increased resistance to mildew, and improved leaf and flower characteristics.

'HYMMAD I' is distinguished from its female parent 'White Wave' by its pure white, mophead inflorescence that does not turn pink or blue in the absence or presence, respectively, of Al. The inflorescence matures a virbrant lime green and maintains the color when utilized as dried flowers. 'HYMMAD I' has lustrous, more leathery, bullate, darker green leaves than 'White Wave'. 'HYMMAD I' had no mildew in late summer, whereas in side-by-side comparisons, 'White Wave' showed 25% infection by mildew. The mophead inflorescence of 'HYMMAD I' is dense, domed-shaped, and the sepals completely cover the fertile flowers whereas the lacecap inflorescence of 'White Wave' has a row of sterile florets around the periphery and fertile flowers in the center.

'HYMMAD I' has better cold resistance than other white mopheads such as 'Regula' ('White Bouquet') (unpatented), 'Schwan' (unpatented) or 'Soeur Thérèsa' (unpatented) and the sterile florets do not have the pink or blue eye of 'Mme Emile Mouillère' (unpatented).

SUMMARY OF THE INVENTION

The following traits have been observed and represent the characteristics of the new cultivar. In combination these characteristics distinguish 'HYMMAD I' from all other varieties in commerce known to the inventor:

1. Pure white flowers (sepals) that are not affected by the presence or absence of Al and hold the color until maturation.
2. At maturation, sepals turn a vibrant lime green and dry to this color.
3. Mophead inflorescences consist of numerous sepals that cover the fertile flowers resulting in a dome of pure white.
4. Rounded habit and strong stems that hold the inflorescences upright.
5. Lustrous, leathery, bullate, dark green leaves.
6. Mildew resistant leaves. Plants of this cultivar have shown greater mildew resistance than all other white mophead varieties of *Hydrangea macrophylla* known to the inventor.

'HYMMAD I' has been asexually propagated in Athens, Ga. since 2002. The characteristics of the cultivar have been stable and reproduced true-to-type in successive vegetative generations.

BRIEF DESCRIPTION OF THE PHOTOGRAPHS

BOTANICAL DESCRIPTION OF THE PLANT

Figure 1:
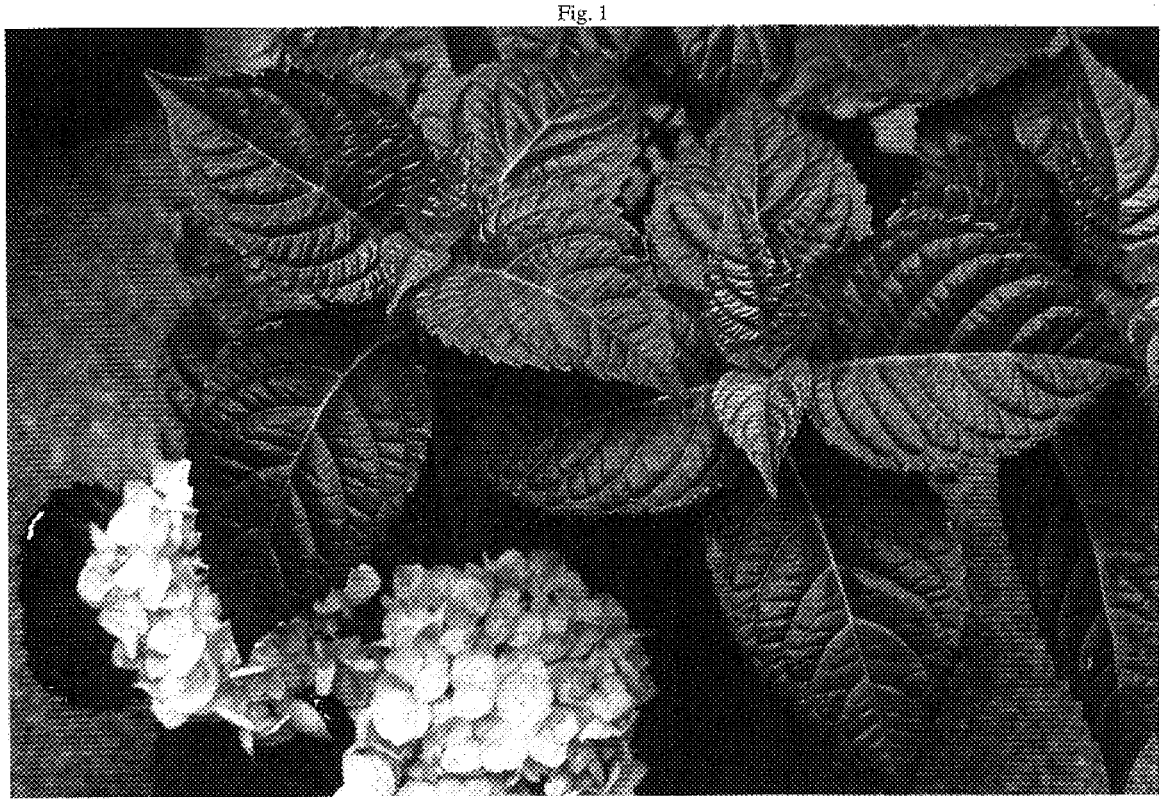
FIG. 1 shows a 2 year-old plant showing the lustrous dark green leaves and opening inflorescences.
Figure 2:
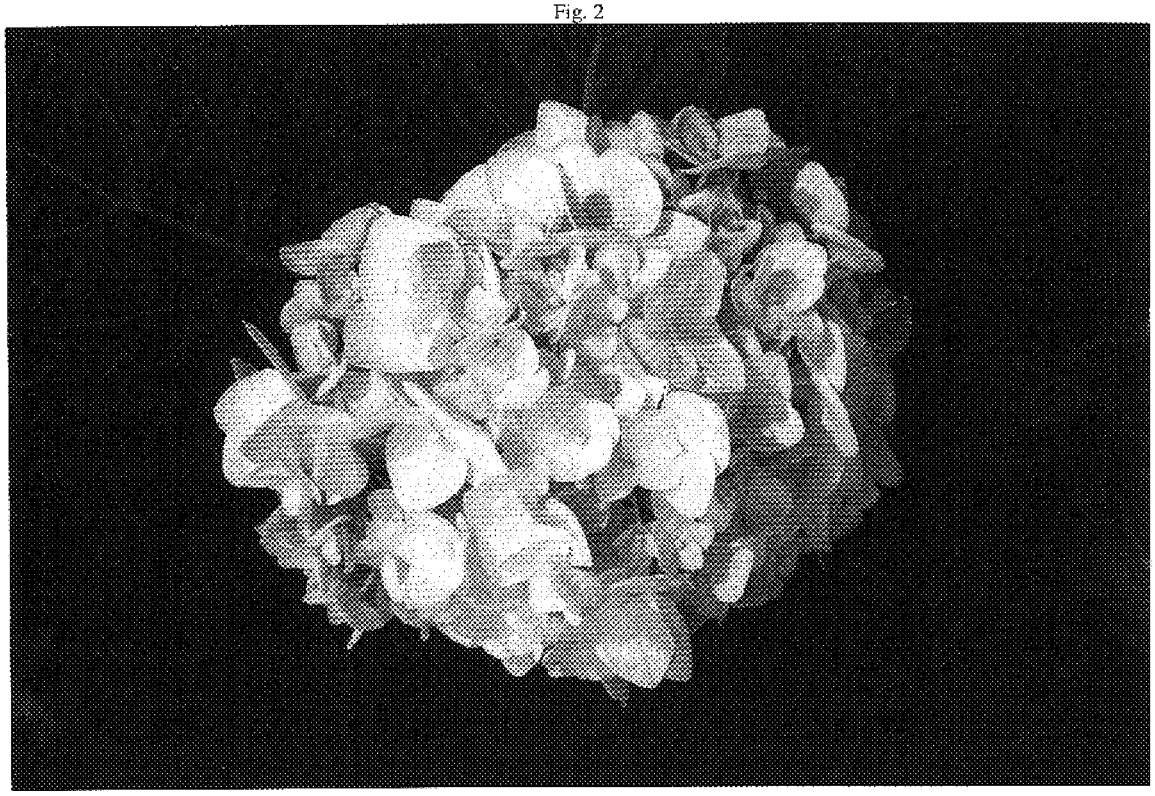
FIG. 2 shows an opening inflorescence.
Figure 3:
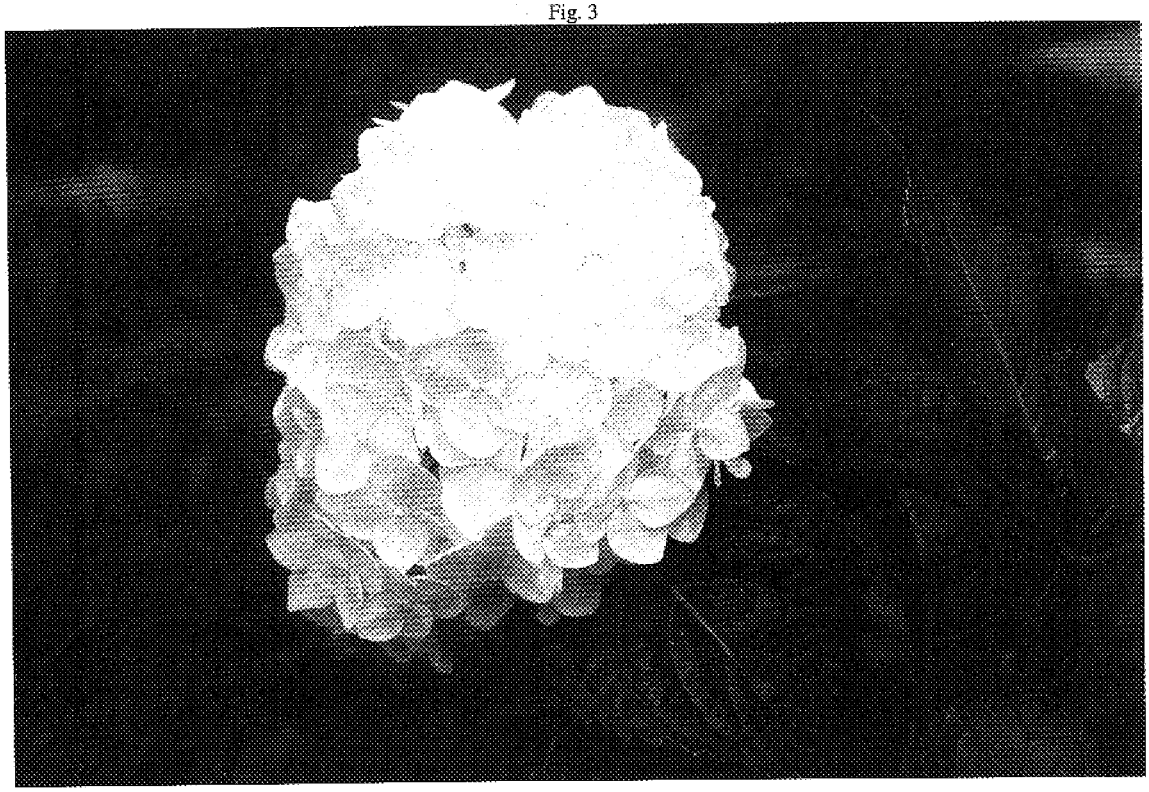
FIG. 3 shows a peak inflorescence showing pure white sepals with no colored eyes.
Figure 4:
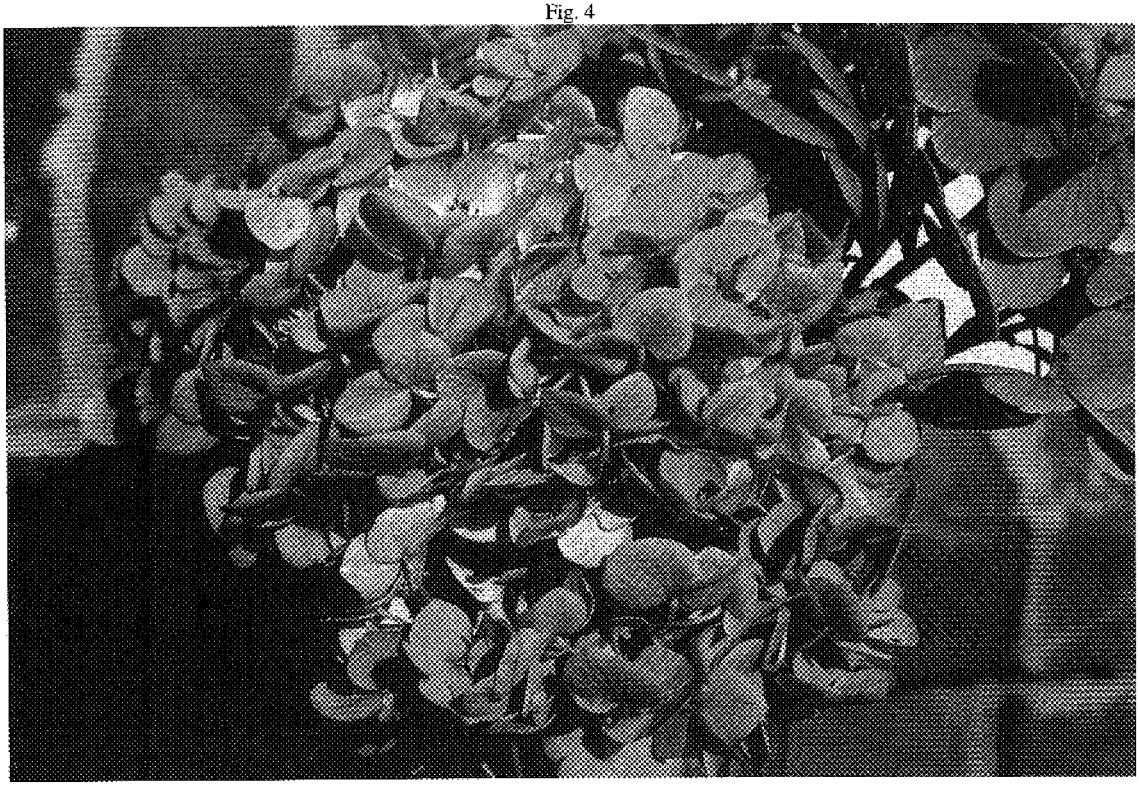
FIG. 4 shows a mature, lime green inflorescence.

A detailed description of *Hydrangea macrophylla* 'HYMMAD I' follows. Colors are based on The Royal Horticultural Colour Chart (1995). All measurements/characteristics were taken from 2 year-old plants growing in 11.8 liter containers under 50% shade at Athens, Ga., USDA Zone 7. Measurements of leaf/stems and floral characteristics are based on 10 to 20 samples. The presence of Al means that the plant was treated with aluminum sulphate (42 g per 3.8 liters of water) applied as a soil drench when flower buds were visible.

Plant: The plant has a compact, upright, rounded growth habit, with upright branches from the base, attaining a size of 28 cm high by 62 cm wide after 2 years.

Stems: Current year stems are round, averaging 3.6 mm in diameter, with no exfoliation and are Greyed-Yellow 161D, Greyed-Orange 165B in color. The average internode length is 5.7 cm. Older stems are 6 mm in diameter, with no pubescence and flaky, and Greyed-Brown N199B, Greyed-Brown N199C in color.

Vegetative buds: The vegetative buds are in an opposite arrangement, 2 per node and flat on the stem. They are globose in shape, 5.5 mm by 2.5 mm, and have 4 scales which are Greyed-Brown 199D in color.

Flower buds: The flower buds are round in shape with no pubescence, 3.5 mm by 3.5 mm by 3 mm, and White 155B in color. They develop in the early summer.

Leaf: The leaves, in opposite arrangement, are ovate in shape with acute base, acuminate apex and serrulate margin. The mature leaf is 9.3 cm long by 6.4 cm wide, very thick, leathery and very waxy. The color of the emerging leaf is Yellow-Green 144A on the upper and Yellow-Green 144B on the lower surfaces, maturing to Green 139A on the upper surface and Green N138C on the lower. The venation is pinnate, with Yellow-Green 146C veins.

The petioles average 2.3 cm long and 3 mm in diameter are grooved above and rounded below, with no pubescence, and are Yellow-Green 144A in color.

Inflorescence: The bloom period is from mid May to the end of June, with the mature, green inflorescence persisting into the fall. The number of flowers in a mophead inflorescence varies widely. The inflorescence averages 12.5 cm in diameter and 8 cm deep.

There are on average 8 inflorescences per plant, one per terminal branch.

Sterile florets: There are typically 4 sepals, sometimes 3, roundish in shape with acute apex, acute base and with a mostly entire margin with an occasional serration. The texture is smooth with no pubescence. The sepals average 16.6 mm long by 16.5 mm wide and the floret is 38 mm by 38 mm. The upper and lower surfaces are white (pure, The R.H.S. Colour Chart contains white with shadings of blue, pink or green, but does not have a pure white) in absence and presence of Al.

The peduncle has no pubescence and is Yellow-Green 144A in color.

The pedicel is finely pubescent, 21 mm in length by 1 mm wide and white in color.

Fertile flowers: The 4 petals per flower are ovate in shape, with acute apex, rounded base and an entire margin. They are 3 mm in length by 1 mm wide, with a smooth texture and no pubsecence. Their color is white.

There are 10 anthers, 1 mm long by 1 mm wide and white 155B in color.

The filament is 3.7 mm long by 0.5 mm wide and white in color.

The superior pistil is globose in shape, 2 mm long by 1 mm wide with no pubescence and white in color.

The stigma is oval, with no pubescence and white in color.

The style is tubular in shape, 1 mm long with no pubescence and white in color.

No ovaries were apparent.

Fruit: The fruit is a capsule, oval in shape, 2 mm long by 1 mm wide, Green 143B in color.

Seed: The seeds are 0.5 mm long by 0.25 mm wide and Greyed-Orange 164C in color.

I claim:

1. A new and distinct variety of *Hydrangea macrophylla* plant substantially as herein described and illustrated.

* * * * *